United States Patent [19]

Welstead, Jr. et al.

[11] 4,143,150
[45] Mar. 6, 1979

[54] DERIVATIVES OF OXANILIC ACID

[75] Inventors: William J. Welstead, Jr., Richmond; Albert D. Cale, Jr., Mechanicsville, both of Va.

[73] Assignee: A. H. Robins Company, Inc., Richmond, Va.

[21] Appl. No.: 826,032

[22] Filed: Aug. 19, 1977

[51] Int. Cl.² .................. C07D 207/14; A61K 31/40
[52] U.S. Cl. ............................ 424/274; 260/326.46; 260/326.47
[58] Field of Search .............. 260/326.46, 326.47; 424/274

[56] References Cited
U.S. PATENT DOCUMENTS

| 3,342,826 | 9/1967 | Meller et al. | 260/326.47 |
| 3,577,440 | 5/1971 | Lunsford et al. | 260/326.47 |
| 3,963,745 | 6/1976 | Cale, Jr. et al. | 424/274 |
| 3,966,957 | 6/1976 | Cale, Jr. et al. | 424/274 |
| 4,002,757 | 1/1977 | Cale, Jr. | 260/326.47 |
| 4,054,591 | 10/1977 | Klaubert et al. | 260/326.47 |

Primary Examiner—Nicholas S. Rizzo
Assistant Examiner—Mary Lee

[57] ABSTRACT

Oxanilic acid derivatives having the formula:

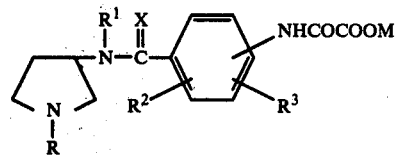

are disclosed wherein R is lower-alkyl, cycloalkyl, phenylalkyl or phenyl; $R^1$ is hydrogen, lower-alkyl or phenyl; $R^2$ is hydrogen, lower-alkyl, or lower-alkoxy; $R^3$ is hydrogen, fluoro, chloro or bromo; X is oxygen or sulfur; and M is hydrogen, lower-alkyl or a physiologically acceptable cation. The compounds are useful for ameliorating and controlling symptoms associated with asthma.

9 Claims, No Drawings

DERIVATIVES OF OXANILIC ACID

BACKGROUND OF THE INVENTION

1. Field of the Invention

The present invention is concerned with derivatives of oxanilic acid and is more particularly concerned with certain 1-substituted-3-pyrrolidinylaminocarbonyl(-and thiocarbonyl-)oxanilic acids, esters and metal salts thereof, compositions containing the same as active ingredients and methods for the production thereof and use of the same.

2. Discussion of the Prior Art

The prior art most closely related to the novel compounds of the present invention are certain N-(1-substituted-3-pyrrolidinyl)benzamides having an amino substituent in the benzamido moiety, said benzamides possessing analgetic, anti-depressant and anti-emetic properties. The compounds are disclosed in U.S. Pat. Nos. 3,577,440; 3,966,957; 3,963,745 and 3,342,826. None of the aforementioned patents or the literature disclose the novel oxanilic acids, esters and metal salts thereof of the present invention.

SUMMARY OF THE INVENTION

The novel 1-substituted-3-pyrrolidinylaminocarbonyl(-and thiocarbonyl-)oxanilic acids, esters and metal salts of the present invention are useful for ameliorating and controlling symptoms associated with asthma and are represented by the formula:

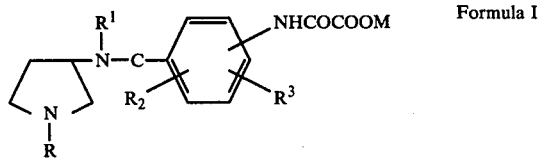

Formula I wherein;
R is lower-alkyl, cycloalkyl, phenylalkyl or phenyl,
$R^1$ is hydrogen, lower-alkyl, or phenyl,
$R^2$ is hydrogen, lower-alkyl, or lower-alkoxy,
$R^3$ is hydrogen, fluoro, chloro, or bromo,
X is oxygen or sulfur, and
M is hydrogen, lower-alkyl, or a physiologically acceptable cation.

The compounds of Formula I may be converted to and are most conveniently employed in the form of non-toxic pharmaceutically acceptable acid addition salts. Such salts also have improved water solubility. The non-toxic pharmaceutically acceptable acid addition salts are those which can be prepared by the use of any suitable inorganic or organic acid. Appropriate acid addition salts are those derived from mineral acids such as hydrochloric acid, hydrobromic acid, sulfuric acid, and phosphoric acid; and organic acids such as acetic, propionic acid, glycolic acid, malonic acid, succinic acid, fumaric acid, malic acid, maleic acid, and tartaric acid.

DETAILED DESCRIPTION OF THE INVENTION

Certain of the novel oxanilic acid compounds of the present invention have been demonstrated to protect sensitized guinea pigs from anaphylactic shock, without concurrently inducing local or systemic side effects. Compounds which are active in protecting guinea pigs from anaphylactic shock have been demonstrated to be generally effective in controlling or ameliorating the symptoms of allergy diseases in humans as, for example, asthma. The compounds of Examples 1 and 2 at a dose level of 50 mg/kg. intraperitoneally prevented anaphylactic shock in horse serum-sensitized guinea pigs.

Guinea pigs of both sexes were sensitized by administering intraperitoneally 1.0 ml. of horse serum followed by a second injection three days later of 0.1 ml. of horse serum by the same route. The guinea pigs were not used for 21 days after being sensitized. The activity of the compounds was determined by administering intraperitoneally minimal doses of each compound to sensitize guinea pigs 30 minutes prior to the intraperitoneal administration of 1.0 ml. of horse serum. When the compounds were given orally the horse serum was given one hour later. The time to death was recorded for each animal. All control animals died within 5 minutes. Five minutes was selected as the cut-off time to indicate the activity of the compounds.

It is therefore a primary object of the present invention to provide novel 1-substituted-3-pyrrolidinylaminocarbonyl (-and thiocarbonyl-)oxanilic acids, esters and metal salts thereof. Another object of the invention is to provide novel 1-substituted-3-pyrrolidinylaminocarbonyl(-and thiocarbonyl-)oxanilic acids, esters and metal salts thereof for ameliorating and controlling symptoms associated with asthma. A still further object is to provide a method of treating allergic phenomena by the internal administration of the novel 1-substituted-3-pyrrolidinylamino carbonyl(-and thiocarbonyl-)oxanilic acids, esters and metal salts thereof of the present invention. Another object is to provide a method for ameliorating and controlling symptoms associated with asthma such as recurrent attacks of paroxysmal dyspnea, wheezing, coughing and a feeling of constriction and other allergic phenomena without currently inducing undesirable side effects by the internal administration of said 1-substituted-3-pyrrolidinylaminocarbonyl(-and thiocarbonyl-)oxanilic acids, esters and metal salts thereof.

In the definition of the symbols in foregoing Formula I, and where they appear elsewhere throughout this specification and claims hereof, the terms have the following significance.

The term "cycloalkyl" as used herein includes primarily cyclic radicals containing three up to eleven carbon atoms inclusive and encompasses such groups as cyclopropyl, cyclobutyl, cyclopentyl, cyclohexyl, methylcyclohexyl, propylcyclohexyl, methylcyclopentyl, ethylcyclohexyl, cycloheptyl, cyclooctyl and cyclododecyl.

The term "phenyl" as used herein encompasses the unsubstituted phenyl radical or a phenyl radical which is substituted by any radical or radicals which are not reactive or otherwise interfering under the conditions or reaction, such as lower alkyl, lower alkoxy, trifluoromethyl, bromo, chloro, fluoro, nitro, and the like. The substituted phenyl radicals have preferably no more than one to three substituents such as those given above and, furthermore, these substituents can be in various available positions of the phenyl nucleus and, when more than one substituent is present, can be the same or different and can be in various position combinations relative to each other. The lower alkyl and lower alkoxy substituents each have preferably from one to four carbon atoms which can be arranged as straight or branched chains. A total of nine carbon atoms in all ring substituents, making a total of fifteen carbon atoms in the radical, is the preferred maximum. Examples of the preferred substituents are methyl, ethyl, propyl, butyl, fluoro, bromo, chloro, methoxy, ethoxy, propoxy, butoxy, and trifluoromethyl radicals.

The term "lower alkyl" as used herein includes straight and branched chain radicals of up to six carbon atoms inclusive, preferably no more than four carbon atoms, and is exemplified by such groups as methyl, ethyl, propyl, isopropyl, butyl, sec. butyl, tertiary butyl, amyl, isoamyl, hexyl, and the like. A "lower alkoxy" group has the formula lower-alkyl-O-.

The term "phenylalkyl" as used herein includes groups such as benzyl, phenethyl, phenpropyl, methylbenzyl, and the like.

METHOD OF PREPARATION

The preparation of the novel oxanilic acids of Formula I may be accomplished by mixing and reacting a selected N-(1-substituted-3-pyrrolidinyl)benzamide or thiobenzamide of Formula II with an alkyl oxalylchloride to give a compound of Formula I wherein the symbol M represents an alkyl group. Basic hydrolysis of the esters of Formula I furnish additional compounds of Formula I wherein M represents a physiologically acceptable cation, said cation being that derived from the basic hydroxide employed. The free acid wherein M is hydrogen is prepared by neutralization of the salt with a mineral acid. The reaction sequence is illustrated by the following:

The procedure for preparing an oxalinate of Formula Ib wherein M is a physiologically acceptable cation is essentially the same as that described hereinabove. Subsequent to the formation of the alkyl oxanilate the organic solution is shaken with an aqueous metallic hydroxide solution until the ester has been hydrolyzed, an organic ether is added to insolubilize the metal oxanilate which is separated by filtration and purified by crystallization from a selected solvent. Alternatively, the alkyl oxanilate is isolated prior to treatment with an aqueous metallic hydroxide solution.

The free acid Ic is readily prepared from the metal salt by acidification of the salt with mineral acid.

The preferred physiologically acceptable cations are the sodium and potassium cations.

The N-(1-substituted-3-pyrrolidinyl)benzamides and thiobenzamides of Formula II used to prepare the novel compounds of the present invention are either disclosed in U.S. Pat. Nos. 3,577,440; 3,963,745 and 3,966,957 or they can be prepared by the procedures described therein.

The following examples are given by way of illustration and are not to be construed as limiting.

EXAMPLE 1

Ethyl 4-(1-cyclohexyl-3-pyrrolidinylaminocarbonyl)oxanilate

To a stirred solution of 10.0 g. (0.037 mole) of 4-amino-N-(1-cyclohexyl-3-pyrrolidinyl)benzamide and 3.7 g. (0.037 mole) of triethylamine and 150 ml. of chlo-

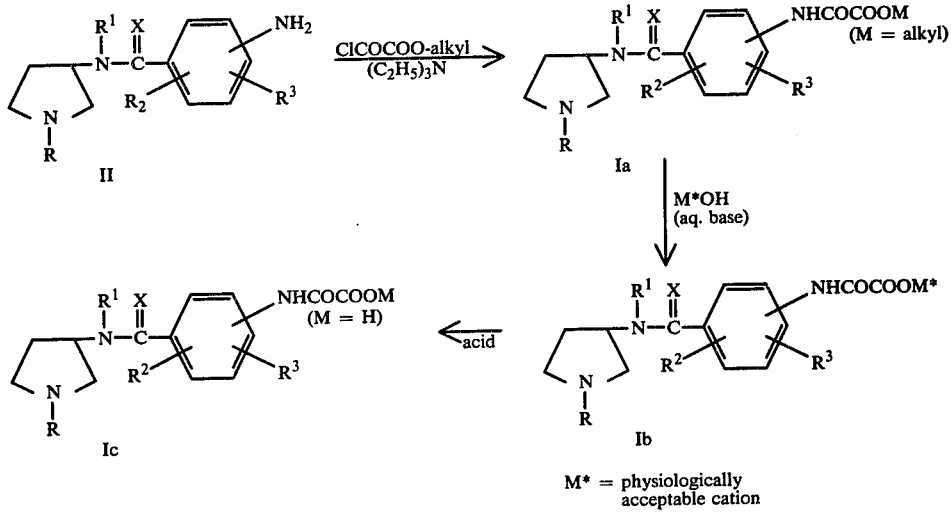

M* = physiologically acceptable cation wherein R, R¹, R², R³ and M are as defined above.

As a general procedure for the preparation of an alkyl 1-substituted-3-pyrrolidinylaminocarbonyl(-or thiocarbonyl-)oxanilate Ia, the following is representative.

A stirred solution of an N-(1-substituted-3-pyrrolidinyl)benzamide or thiobenzamide of Formula II in a dry organic solvent, e.g., chloroform containing a suitable acid acceptor as, for example, triethylamine is treated dropwise with an alkyl oxalylchloride with ice bath cooling. The reaction mixture is then stirred at ambient temperature for a period of time to insure that the reaction is essentially complete and is then shaken with a dilute aqueous carbonate solution. The separated organic layer is dried and concentrated under reduced pressure to give a residual solid which is crystallized from a suitable solvent.

roform was added dropwise 5.0 g. (0.037 mole) of ethyl oxalyl chloride with ice-bath cooling. Stirring was continued overnight. The solution was washed with a potassium carbonate solution, the chloroform layer separated, dried, filtered, and concentrated in vacuo. The residue crystallized on trituration with isopropyl ether and was recrystallized from ethyl acetate. The product weighed 4.6 g. (32%) and melted at 138°–141° C.

Analysis: Calculated for $C_{21}H_{29}N_3O_4$: C,65.10; H,7.54; N,10.84; Found: C,64.83; H,7.45; N,10.63.

EXAMPLE 2

Potassium 4-(1-cyclohexyl-3-pyrrolidinylaminocarbonyl)oxanilate

To a stirred mixture of 12.0 g. (0.039 mole) of 4-amino-N-(1-cyclohexyl-3-pyrrolidinyl)benzamide and 4.3 g. (0.043 mole) of triethylamine in 50 ml. of chloroform was slowly added 5.9 g. (0.043 mole) of ethyl oxalylchloride. After two hours stirring 4.3 g. of triethylamine was added, followed by the addition of 5.9 g. of ethyl oxalylchloride. The solution was stirred 18 hours and then shaken with 200 ml. of dilute potassium hydroxide solution. About 200 ml. of isopropyl ether was added and the shaking was continued. The mixture was filtered and the solid residue was recrystallized three times from ethanol-water to give 5.5 g. of product. The material did not melt when heated to 345° C.; however, darkening occurred above 295° C.

Analysis: Calculated for $C_{19}H_{24}N_3O_4K$: C,57.41; H,6.09; N,10.57; Found: C,57.04; H,6.09; N,10.42.

EXAMPLE 3

When in the procedure of Example 1 and in the manner of the preceding discussion, 4-amino-N-(1-cyclohexyl-3-pyrrolidinyl)benzamide is replaced by equal moler amounts of:

4-amino-N-methyl-N-(1-phenyl-3-pyrrolidinyl)benzamide, 4-amino-N-(1-phenyl-3-pyrrolidinyl)benzamide, 4-amino-N-butyl-N-(1-phenyl-3-pyrrolidinyl)benzamide, 4-amino-5-chloro-2-methoxy-N-(1-methyl-3-pyrrolidinyl) benzamide, 4-amino-N-methyl-N-(1-cyclohexyl-3-pyrrolidinyl)benzamide, 4-amino-5-chloro-2-methoxy-N-(1-cyclohexyl-3-pyrrolidinyl)benzamide, 4-amino-5-chloro-2-methoxy-N-methyl-N-(1-cyclohexyl-3-pyrrolidinyl)benzamide, 4-amino-N-methyl-N-(1-cyclohexyl-3-pyrrolidinyl)thiobenzamide, 4-amino-N-methyl-N-(1-cyclododecyl-3-pyrrolidinyl)benzamide, 4-amino-N-methyl-N-(1-cyclopentyl-3-pyrrolidinyl)benzamide, 4-amino-N-(1-benzyl-3-pyrrolidinyl)benzamide, 4-amino-N-phenyl-N-(1-cyclohexyl-3-pyrrolidinyl)benzamide, 4-amino-2-ethyl-N-(1-cyclohexyl-3-pyrrolidinyl)benzamide, 4-amino-N-(1-phenyl-3-pyrrolidinyl)thiobenzamide, and 4-amino-2-ethyl-N-(1-methyl-3-pyrrolidinyl)thiobenzamide, there are obtained, ethyl 4-(1-phenyl-3-pyrrolidinyl-N-methylaminocarbonyl)oxanilate, ethyl 4-(1-phenyl-3-pyrrolidinylaminocarbonyl)oxanilate, ethyl 4-(1-phenyl-3-pyrrolidinyl-N-butylaminocarbonyl)oxanilate, ethyl 4-(1-methyl-3-pyrrolidinylaminocarbonyl)-5-chloro-2-methoxyoxanilate, ethyl 4-(1-cyclohexyl-3-pyrrolidinyl-N-methylaminocarbonyl)oxanilate, ethyl 4-(1-cyclohexyl-3-pyrrolidinylaminocarbonyl)-5-chloro-2-methoxyoxanilate, ethyl 4-(1-cyclohexyl-3-pyrrolidinyl-N-methylaminocarbonyl)-5-chloro-2-methoxyoxanilate, ethyl 4-(1-cyclohexyl-3-pyrrolidinyl-N-methylaminothiocarbonyl)oxanilate, ethyl 4-(1-cyclododecyl-3-pyrrolidinyl-N-methylamino carbonyl)oxanilate, ethyl 4-(1-cyclopentyl-3-pyrrolidinyl-N-methylaminocarbonyl)oxanilate, ethyl 4-(1-benzyl-3-pyrrolidinylaminocarbonyl)oxanilate, ethyl 4-(1-cyclohexyl-3-pyrrolidinyl-N-phenylaminocarbonyl)oxanilate, ethyl 4-(1-cyclohexyl-3-pyrrolidinylaminocarbonyl)-2-ethyl oxanilate, ethyl 4-(1-phenyl-3-pyrrolidinylaminothiocarbonyl)oxanilate, and ethyl 4-(1-methyl-3-pyrrolidinylaminothiocarbonyl)-2-ethyloxanilate.

EXAMPLE 4

Ethyl 2-(1-cyclohexyl-3-pyrrolidinylaminocarbonyl)oxanilate Hydrochloride

To a stirred solution of 10.4 g. (0.0363 mole) of 2-amino-N-(1-cyclohexyl-3-pyrrolidinyl)benzamide and 3.72 g. (0.037 mole) of triethylamine in 150 ml. of dry chloroform was added dropwise 4.9 g. (0.036 mole) of ethyl oxalylchloride. After addition, the stirred solution was refluxed 1.5 hrs. and then allowed to stand overnight at room temperature. The solution was washed twice with cold water and then extracted with 125 ml. of cold (5° C.) 3N hydrochloric acid. The acidic aqueous solution gave 3.62 g. (35.2%) of 2-amino-N-(1-cyclohexyl-3-pyrrolidinyl)benzamide. Concentration of the chloroform solution gave 12.45 g. (81.2%) of crude product as the hydrochloride salt. The product was crystallized from ethanol-ether to give 9.93 g. of product which melted at 136°-139° C.

EXAMPLE 5

Sodium 2-(1-cyclohexyl-3-pyrrolidinylaminocarbonyl)oxanilate

A stirred solution of 4.2 g. of ethyl 2-(1-cyclohexyl-3-pyrrolidinylaminocarbonyl)oxanilate hydrochloride in 20 ml. of 50% aqueous ethanol was treated dropwise with 19.5 ml. of 1.03 N sodium hydroxide. After thirty minutes the solution was heated to 50° C. and poured into 130 ml. of boiling ethanol. After the mixture cooled to room temperature it was kept at 4° C. for two days and the amorphous sodium salt was collected by filtration.

EXAMPLE 6

2-(1-Cyclohexyl-3-pyrrolidinylaminocarbonyl)oxanilic Acid

The amorphous sodium salt from Example 5 was suspended in distilled water; the pH of the solution was 9.0. The stirred solution was cooled and acidified with dilute hydrochloric acid to pH 4 at which point maximum precipitation occurred. The precipitate was collected and air-dried to give 2.76 g. of product which melted at 268°-270° C.

FORMULATION AND ADMINISTRATION

The invention further provides pharmaceutical compositions, comprising as active ingredient, at least one of the compounds according to the invention in association with a pharmaceutical carrier or excipient. The compounds may be presented in a form suitable for oral, parenteral or intramuscular administration, or in a form suitable for inhalation. Thus, for example, compositions for oral administration are solid or liquid and can take the form of capsules, tablets, coated tablets, suspensions, etc., employing such carriers or excipients conveniently used in the pharmaceutical art. Suitable tableting excipients include lactose, potato and maize starches, talc, gelatin and stearic and silicic acids, magnesium stearate and polyvinyl pyrrolidone.

For parenteral administration, the carrier or excipient can be a sterile, parenterally acceptable liquid, e.g., water, or a parenterally acceptable oil, e.g., arachis oil, contained in ampoules.

Advantageously, the compositions are formulated as dosage units, each unit being adapted to supply a fixed effective dose of active ingredient. Although very small quantities of the active materials of the present invention are effective when minor therapy is involved or in cases of administration to subjects having a relatively low body weight, unit dosages are usually from 5 milligrams or above and preferably 25, 50 or 100 milligrams or even higher, depending of course upon the emergency of the situation and the particular result desired. Five to 50 milligrams appears optimum per unit dose, or usual broader ranges appear to be 1 to 100 milligrams per unit dose. Daily dosages should preferably range from 10 mg. to 100 mg. It is only necessary that the active ingredient constitute an effective amount, i.e., such that a suitable effective dosage will be obtained, consistent with the dosage form employed. Obviously, several unit dosage forms may be administered at about the same time.

| CAPSULES | |
|---|---|
| Ingredients: | Per cap., mg. |
| 1. Active ingredient | 5.0 |
| 2. Lactose | 140.0 |
| 3. Magnesium stearate | 4.0 |

Procedure:

(1) Blend 1, 2 and 3.
(2) Mill this blend and blend again.
(3) This milled blend is then filled into No. 1 hard gelatin capsules.

| TABLETS | |
|---|---|
| Ingredients: | Mg./tabl., mg. |
| 1. Active ingredient | 5.0 |
| 2. Corn starch | 20.0 |
| 3. Kelacid | 20.0 |
| 4. Keltose | 20.0 |
| 5. Magnesium stearate | 1.5 |

Procedure:

(1) Blend 1, 2, 3 and 4.
(2) Add sufficient water portionwise to the blend from step No. 1 with careful stirring after each addition. Such additions of water and stirring continue until the mass is of a consistency to permit its conversion to wet granules.
(3) The wet mass is converted to granules by passing it through the oscillating granulator, using 8-mesh screen.
(4) The wet granules are then dried in an oven at 140° F.
(5) The dried granules are then passed through an oscillating granulator, using a 10-mesh screen.
(6) Lubricate the dry granules with 0.5% magnesium stearate.
(7) The lubricated granules are compressed on a suitable tablet press.

| INTRAVENOUS INJECTION | |
|---|---|
| Ingredients: | |
| 1. Active ingredient | mg. 5.0 |
| 2. pH 4.0 buffer solution, q.s. to | ml. 1.0 |

Procedure:

(1) Dissolve the active ingredient in the buffer solution.
(2) Aseptically filter the solution from Step No. 1.
(3) The sterile solution is now aseptically filled into sterile ampoules.
(4) The ampoules are sealed under aseptic conditions.

| INTRAMUSCULAR INJECTION | |
|---|---|
| Ingredients: | |
| 1. Active ingredient | mg. 5.0 |
| 2. Isotonic buffer solution 4.0, q.s. to | ml. 2.0 |

Procedure:

(1) Dissolve the active ingredient in the buffer solution.
(2) Aseptically filter the solution from Step No. 1.
(3) The sterile solution is now aseptically filled into sterile ampoules.
(4) The ampoules are sealed under aseptic conditions.

| INHALATION | |
|---|---|
| Ingredients: | |
| 1. Active ingredients | mg. 100 |
| 2. Alcohol 95%, q.s. | cc. 1.0 |

Procedure:

(1) Dissolve No. 1 and No. 2.
(2) This solution is properly packaged in an aerosol dispenser containing a metered valve and suitable propellant.

What is claimed is:

1. A compound selected from those having the formula:

[Structural formula: a pyrrolidine/piperidine ring with $N-R$ substituent, connected via $N-R^1$ to $C(=X)$ group attached to a benzene ring bearing $R^2$, $R^3$ and NHCOCOOM substituents]

wherein R is lower-alkyl, cycloalkyl, phenylalkyl, alkylphenylalkyl, phenyl or substituted phenyl having one to three substituents selected from lower-alkyl, lower-alkoxy, trifluoromethyl, bromo, chloro, fluoro and nitro groups, $R^1$ is hydrogen, lower-alkyl, phenyl or substituted phenyl having one to three substituents selected from lower-alkyl, lower-alkoxy, trifluoromethyl, bromo, chloro, fluoro and nitro groups, $R^2$ is hydrogen, lower-alkyl, or lower alkoxy, $R^3$ is hydrogen, fluoro, chloro or bromo, X is oxygen or sulfur, and M is hydrogen, lower-alkyl or a physiologically acceptable cation.

2. The compound of claim 1 which is ethyl 4-(1-cyclohexyl-3-pyrrolidinylaminocarbonyl)oxanilate.

3. The compound of claim 1 which is potassium 4-(1-cyclohexyl-3-pyrrolidinylaminocarbonyl)oxanilate.

4. A composition useful for its anti-allergy effect comprising an effective amount of about one to 100 milligrams of (a) a compound of the formula:

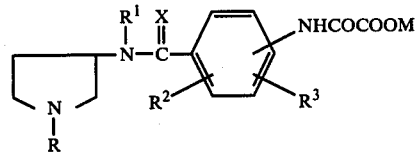

wherein R is lower-alkyl, cycloalkyl, phenylalkyl, alkylphenylalkyl, phenyl or substituted phenyl having one to three substituents selected from lower-alkyl, lower-alkoxy, trifluoromethyl, bromo, chloro, fluoro and nitro groups, $R^1$ is hydrogen, lower-alkyl, phenyl or substituted phenyl having one to three substituents selected from lower-alkyl, lower-alkoxy, trifluoromethyl, bromo, chloro, fluoro and nitro groups, $R^2$ is hydrogen, lower-alkyl, or lower alkoxy, $R^3$ is hydrogen, fluoro, chloro or bromo, X is oxygen or sulfur, M is hydrogen, lower-alkyl, or a physiologically acceptable cation, and (b) a pharmaceutically acceptable carrier.

5. A composition of claim 4 wherein the compound is ethyl 4-(1-cyclohexyl-3-pyrrolidinylaminocarbonyl)oxanilate.

6. A composition of claim 4 wherein the compound is potassium 4-(1-cyclohexyl-3-pyrrolidinylaminocarbonyl)oxanilate.

7. A process which comprises administering to a living animal body for its anti-allergy effect an effective amount of a compound of the formula:

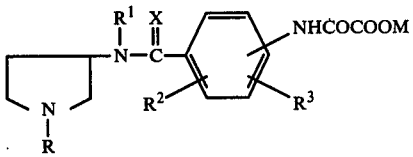

wherein R is lower-alkyl, cycloalkyl, phenylalkyl, alkylphenylalkyl phenyl or substituted phenyl having one to three substituents selected from lower-alkyl, lower-alkoxy, trifluoromethyl, bromo, chloro, fluoro and nitro groups, $R^1$ is hydrogen, lower-alkyl, phenyl or substituted phenyl having one to three substituents selected from lower-alkyl, lower-alkoxy, trifluoromethyl, bromo, chloro, fluoro and nitro groups, $R^2$ is hydrogen, lower-alkyl, or lower alkoxy, $R^3$ is hydrogen, fluoro, chloro or bromo, X is oxygen or sulfur, and M is hydrogen, lower-alkyl or a physiologically acceptable cation.

8. A process of claim 7 wherein the compound is ethyl 4-(1-cyclohexyl-3-pyrrolidinylaminocarbonyl)oxanilate.

9. A process of claim 7 wherein the compound is potassium 4-(1-cyclohexyl-3-pyrrolidinylaminocarbonyl)oxanilate.

* * * * *